United States Patent
Lewis et al.

(10) Patent No.: US 9,939,386 B2
(45) Date of Patent: Apr. 10, 2018

(54) SYSTEMS AND METHODS FOR SAMPLE INSPECTION AND REVIEW

(71) Applicant: KLA-Tencor Corporation, Milpitas, CA (US)

(72) Inventors: Isabella T. Lewis, San Jose, CA (US); Yakov Bobrov, Burlingame, CA (US)

(73) Assignee: KLA—Tencor Corporation, Milpitas, CA (US)

( * ) Notice: Subject to any disclaimer, the term of this patent is extended or adjusted under 35 U.S.C. 154(b) by 355 days.

(21) Appl. No.: 13/779,062

(22) Filed: Feb. 27, 2013

(65) Prior Publication Data
US 2013/0271596 A1 Oct. 17, 2013

Related U.S. Application Data

(60) Provisional application No. 61/623,264, filed on Apr. 12, 2012.

(51) Int. Cl.
*G01N 21/88* (2006.01)
*G01N 21/95* (2006.01)

(52) U.S. Cl.
CPC ..... *G01N 21/8806* (2013.01); *G01N 21/9501* (2013.01); *G01N 2021/8845* (2013.01)

(58) Field of Classification Search
CPC ........... G01N 21/8806; G01N 21/9501; G01N 2021/8845

(Continued)

(56) References Cited

U.S. PATENT DOCUMENTS 5,150,043 A * 9/1992 Flesner ................. B82Y 15/00 324/750.14
5,625,193 A 4/1997 Broude et al.
(Continued)

FOREIGN PATENT DOCUMENTS

JP H07-306153 6/1997
JP 2000105203 A 4/2000
(Continued)

OTHER PUBLICATIONS

Peter Green, Simple, Efficient, High-Brightness-LED Control, Bodo's Power Systems, www.bodospower.com, May 2007, Found online at: http://www.irf.com/technical-info/whitepaper/bp_05-07_ir_online.pdf.

(Continued)

*Primary Examiner* — Tung Vo
*Assistant Examiner* — Zaihan Jiang
(74) *Attorney, Agent, or Firm* — Suiter Swantz pc llo

(57) ABSTRACT

The disclosure is directed to systems and methods for sample inspection and review. In some embodiments, images are collected and/or defects are located utilizing separately addressable red, green, and blue (RGB) illumination sources to improve image quality. In some embodiments, illumination sources are pulse width modulated for substantially consistent light intensity in presence of variable sample motion. In some embodiments, a stage assembly is configured to support the sample without blocking access to the supported surface of the sample, and further configured to reduce oscillations or vibrations of the sample. In some embodiments, an illumination system includes an imaging path and a focusing path to allow full field of view focusing.

35 Claims, 8 Drawing Sheets

(58) Field of Classification Search
USPC .......................................................... 348/126
See application file for complete search history.

(56) References Cited

U.S. PATENT DOCUMENTS

| | | | |
|---|---|---|---|
| 5,744,800 A * | 4/1998 | Kakibayashi et al. ......... | 250/311 |
| 5,889,593 A * | 3/1999 | Bareket .......................... | 356/445 |
| 6,201,601 B1 * | 3/2001 | Vaez-Iravani ............. | G01J 3/44 |
| | | | 356/237.4 |
| 6,401,008 B1 | 6/2002 | Ehrichs et al. | |
| 6,407,373 B1 | 6/2002 | Dotan | |
| 7,417,724 B1 | 8/2008 | Sullivan et al. | |
| 7,709,794 B2 * | 5/2010 | Zhao ....................... | G01N 25/72 |
| | | | 250/334 |
| 2001/0012393 A1 | 8/2001 | Yonezawa | |
| 2002/0028399 A1 * | 3/2002 | Nakasuji ............... | G01N 23/225 |
| | | | 430/30 |
| 2002/0030812 A1 | 3/2002 | Ortyn et al. | |
| 2002/0033449 A1 * | 3/2002 | Nakasuji ............... | G01N 23/225 |
| | | | 250/306 |
| 2003/0133604 A1 * | 7/2003 | Neumann ..................... | 382/149 |
| 2003/0218741 A1 | 11/2003 | Guetta | |
| 2004/0146295 A1 * | 7/2004 | Furman .............. | G01N 21/8806 |
| | | | 398/9 |
| 2005/0045821 A1 * | 3/2005 | Noji ..................... | G01N 23/225 |
| | | | 250/311 |
| 2005/0199807 A1 * | 9/2005 | Watanabe et al. ............ | 250/306 |
| 2006/0017807 A1 * | 1/2006 | Lee ........................... | B60R 1/00 |
| | | | 348/36 |
| 2006/0203231 A1 * | 9/2006 | Uto et al. ................... | 356/237.2 |
| 2007/0117225 A1 * | 5/2007 | Capaldo et al. ................ | 438/14 |
| 2007/0121106 A1 | 5/2007 | Shibata et al. | |
| 2008/0204738 A1 | 8/2008 | Schupp et al. | |
| 2010/0091272 A1 | 4/2010 | Asada et al. | |
| 2011/0075151 A1 * | 3/2011 | Jeong ................... | G01N 21/956 |
| | | | 356/453 |
| 2011/0104830 A1 | 5/2011 | Kimba et al. | |
| 2011/0255081 A1 * | 10/2011 | De Greeve ........ | G01N 21/8914 |
| | | | 356/237.2 |
| 2012/0013899 A1 | 1/2012 | Amanullah | |
| 2013/0062536 A1 * | 3/2013 | Bardos ............... | G01N 21/6489 |
| | | | 250/459.1 |

FOREIGN PATENT DOCUMENTS

| | | |
|---|---|---|
| JP | H11-311608 | 5/2001 |
| JP | 200517805 A | 8/2006 |
| JP | 2009523244 A | 6/2009 |
| TW | 200827709 A | 7/2008 |
| TW | 201144747 A | 12/2011 |
| TW | I356568 B | 1/2012 |

OTHER PUBLICATIONS

European Search Report for EP 13775290.3 dated Nov. 30, 2015, 8 pages.

* cited by examiner

SYSTEMS AND METHODS FOR SAMPLE INSPECTION AND REVIEW

PRIORITY

The present application claims priority to U.S. Provisional Application Ser. No. 61/623,264, entitled WAFER BACKSIDE INSPECTION AND HIGH RESOLUTION OPTICAL REVIEW, By Isabella Lewis et al., filed Apr. 12, 2012.

TECHNICAL FIELD

The present disclosure generally relates to the field of sample inspection and review in semiconductor fabrication or testing.

BACKGROUND

It is useful to analyze the backside of a sample, such as a semiconductor wafer, at various stages in fabrication and/or testing of semiconductor devices. One technique for obtaining high resolution images of a wafer backside is to physically flip over the wafer and collect images utilizing a state of the art review system. However, doing so can destroy front side features of the wafer. This makes backside review impractical for a wafer that is nearly complete and potentially still yielding die.

Review images are typically collected utilizing a Bayer filter collection scheme. Red, green, and blue filters are placed above each pixel to create a color checkerboard. Then a color image can be reconstructed by interpolating red, green, and blue values for each point. A second method, generally accepted to give superior images to the Bayer camera, is a "3-chip camera". These cameras incorporate means for color separation, such as a prism, at the input of the camera and split red, green, and blue illumination to 3 separate focal planes. Both of these prior methods work with "white light" illumination (e.g. broadband halogen bulbs or white LEDs) to take RGB images.

The Bayer filter camera setup can result in "checkerboard" artifacts caused by interpolation of the image needed to fill in the full image in RGB color. The interpolation error can be minimized by designing for more pixels over the optical resolution (or Airy pattern)—but doing so increases the pixel count of the camera or results in a decreased field of view. The 3-chip camera is unattractive for size, cost, and optical aberrations caused by the color separation. The aberrations may include one or more of: astigmatism due to the air gap in the separation prism, TIR loss "striping features" due to the air gap in the prism, relative focus errors due to manufacturing tolerances for Z position of the chips, and variations in distortion due to prism manufacturing tolerances that cause lateral color features that vary between colors.

SUMMARY

The present disclosure is directed to inspection and/or review systems that cure deficiencies in the current state of the art.

An embodiment of the present disclosure includes a system for analyzing a sample utilizing one or more illumination sources configured to sequentially illuminate a surface of the sample with red, green, and blue illumination. The system further includes one or more detectors configured to receive illumination reflected from the surface of the sample in response to the illumination by the one or more illumination sources. At least one computing system in communication the one or more detectors is configured to reconstruct a color image of a portion of the surface of the sample from a first image associated with the red illumination, a second image associated with the green illumination, and a third image associated with the blue illumination, sequentially collected utilizing the one or more detectors of the review module.

Another embodiment includes a system for analyzing a sample that may be vibrating or oscillating due to various environmental forces. The system includes a stage configured to support the wafer by contacting a selected number of points on a surface of the sample and at least one sidearm configured to contact a selected number of points along an edge of the sample. The system further includes one or more illumination sources configured to illuminate the surface of the sample. The system further includes one or more detectors configured to receive illumination reflected from the surface of the sample in response to the illumination by the one or more illumination sources. At least one computing system in communication the one or more detectors is configured to determine information associated with a defect of the sample utilizing information associated with the illumination received by the one or more detectors.

Another embodiment includes a system for analyzing a sample with an imaging path and a focusing path. The system includes a first illumination source configured to provide illumination along a first illumination path to a surface of the sample. The system further includes a second illumination source configured to provide illumination along a second illumination path to the surface of the sample, where the second illumination path includes a grid mask utilized to focus of one or more detectors of the system. The one or more detectors are configured to receive illumination reflected from the surface of the sample in response to the illumination at least one of the first illumination source and the second illumination source. At least one computing system in communication the one or more detectors is configured to determine a focus position based upon a portion of illumination from the second illumination source reflected from the surface of the sample to the one or more detectors.

At least a portion of one embodiment may be combined with at least a portion of another embodiment to arrive at further embodiments of the disclosure. For example, another embodiment of the disclosure includes a system for inspection and review of a sample. The system includes an inspection module including: one or more illumination sources configured to sequentially illuminate a surface of the sample with red, green, and blue illumination, and one or more monochromic detectors configured to receive illumination reflected from the surface of the sample in response to the sequential illumination by the one or more illumination sources. The system further includes a review module including: one or more illumination sources configured to illuminate the surface of the sample, and one or more detectors configured to receive illumination reflected from the surface of the sample in response to the illumination by the one or more illumination sources. At least one computing system in communication with the inspection module and the review module is configured to determine a location of a defect of the sample utilizing information associated with the illumination received by the one or more monochromic detectors of the inspection module. The computing system is further configured to collect an image of a portion of the surface of the sample including the defect utilizing the one or more detectors of the review module and the determined location of the defect.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1:
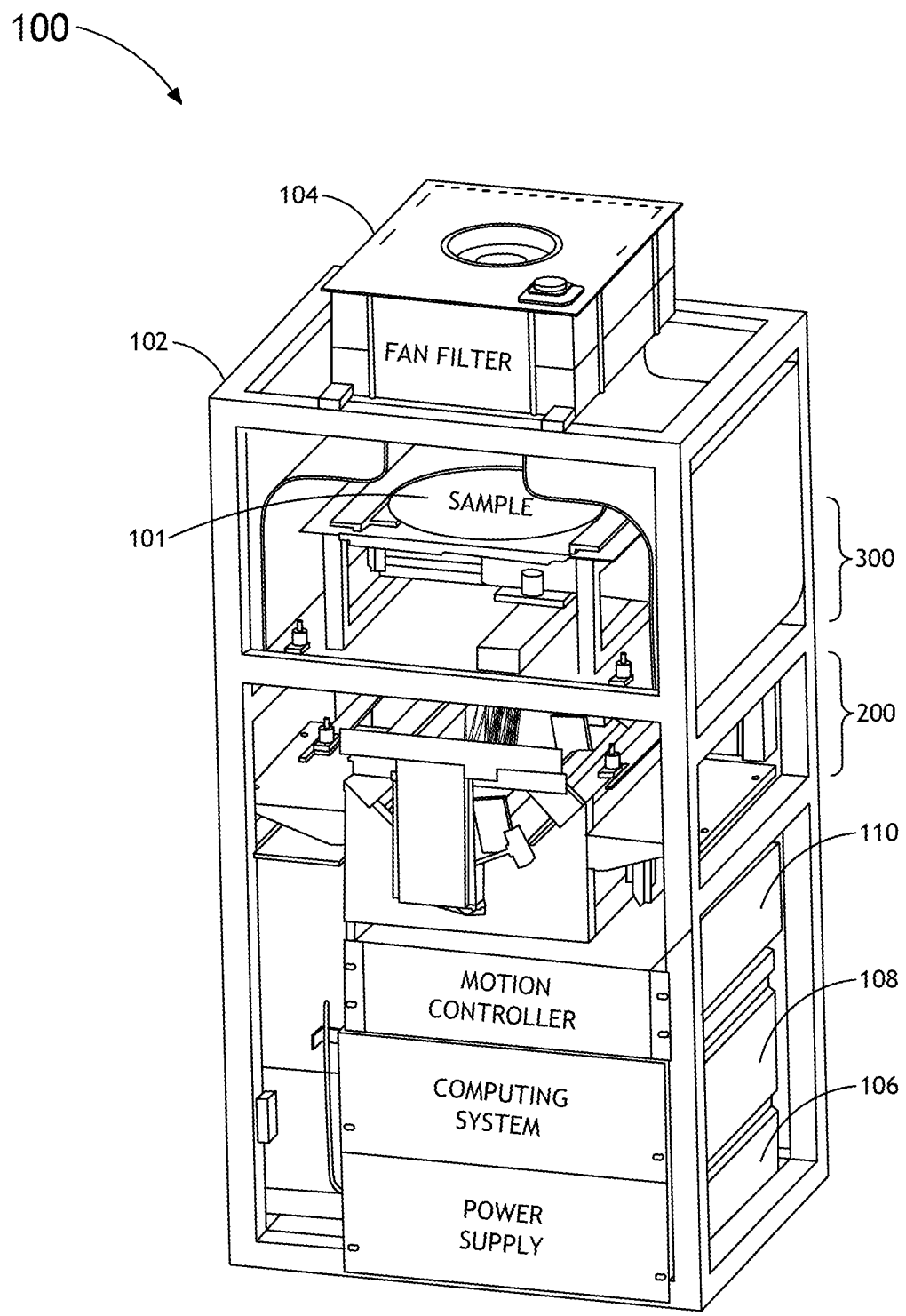
FIG. 1 illustrates a system for inspection and review of a sample, in accordance with an embodiment of this disclosure.

FIG. 1 illustrates a system 100 for analyzing a sample 101, such as a semiconductor wafer. In an embodiment, the system 100 may include a first (inspection) module 200 for inspecting a surface of the sample 101 to locate one or more defects and a second (review) module 300 for imaging at least a portion of the surface of the sample 101 including the one or more located defects. The system 100 may further include at least one computing system 108 in communication with the inspection module 200 and/or the review module 300. According to various embodiments, the computing system 108 may include one or more processors configured to execute program instructions stored by at least one carrier medium to perform one or more of the steps or functions described herein.

In some embodiments, the system 100 further includes a frame 102 configured to support the inspection module 200 and the review module 300. The frame 102 may be further configured to support the computing system 108 and a power supply 106 for providing or distributing electrical power among various components of the system 100. In some embodiments, the system 100 further includes a motion controller 110 driven by the computing system 108. The motion controller 110 may be configured to control one or more actuation means, such as a motor or servo, of the inspection module 200 and/or the review module 300 in response to electrical signals or instructional data received from the computing system 108. In some embodiments, the system 100 further includes a filtration unit 104, such as a fan based exhaust system, configured to filter the atmosphere of the inspection module 200 and/or review module 300.

In some embodiments, the system 100 is configured for inspecting and reviewing the backside surface of the sample 101 without damaging the front side surface features (e.g. various semiconductor and non-semiconductor layers or films). Accordingly, the inspection module 200 and/or the review module 300 may include a stage assembly configured to support the sample 101 in a manner that provides access to a substantial entirety (e.g. more than 80%) of the backside surface without making harmful contact with the front side of the sample 101. Various embodiments illustrating constructions of the stage assembly are illustrated in further detail below.

In some embodiments, the review module 300 may be configured to fit into a vertical slice of the inspection module 200. In some embodiments, a single-swath or multiple-swath (e.g. up to 10 swaths) inspection architecture combined with the small size of the review module 300 (e.g. <300 mm) may allow the full inspection-review module 200 and 300 to fit into a 550 mm module depth. The foregoing embodiments are included for illustrative purposes only and should not be construed as limitations of the disclosure. It is contemplated that various dimensions and ranges will be implemented according to desired specifications or application requirements.

Figure 2A:
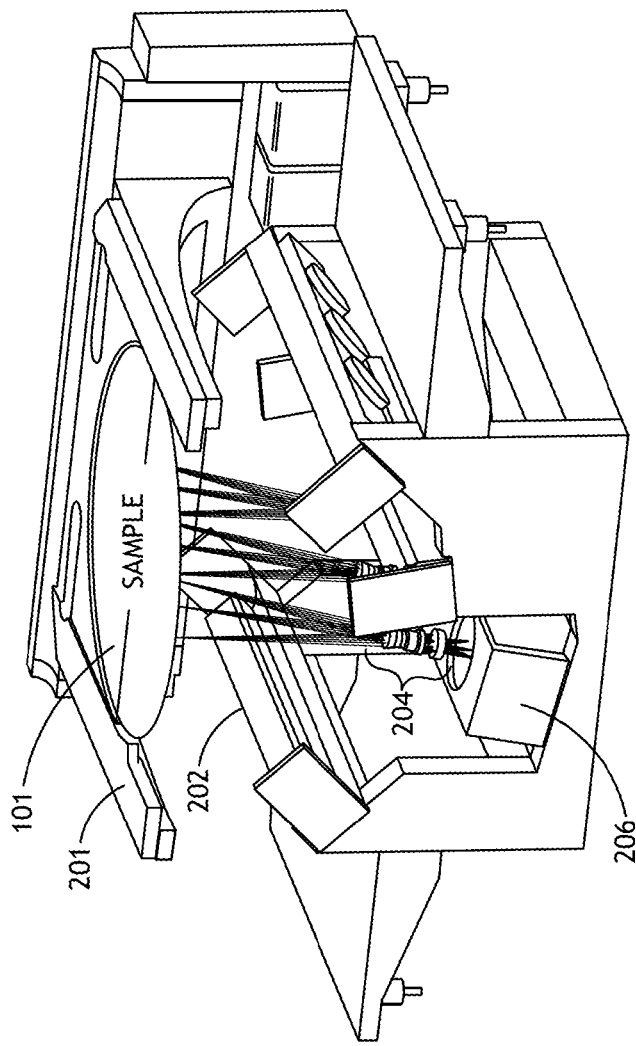
FIG. 2A illustrates a system for inspecting a sample, in accordance with an embodiment of this disclosure.
Figure 2B:
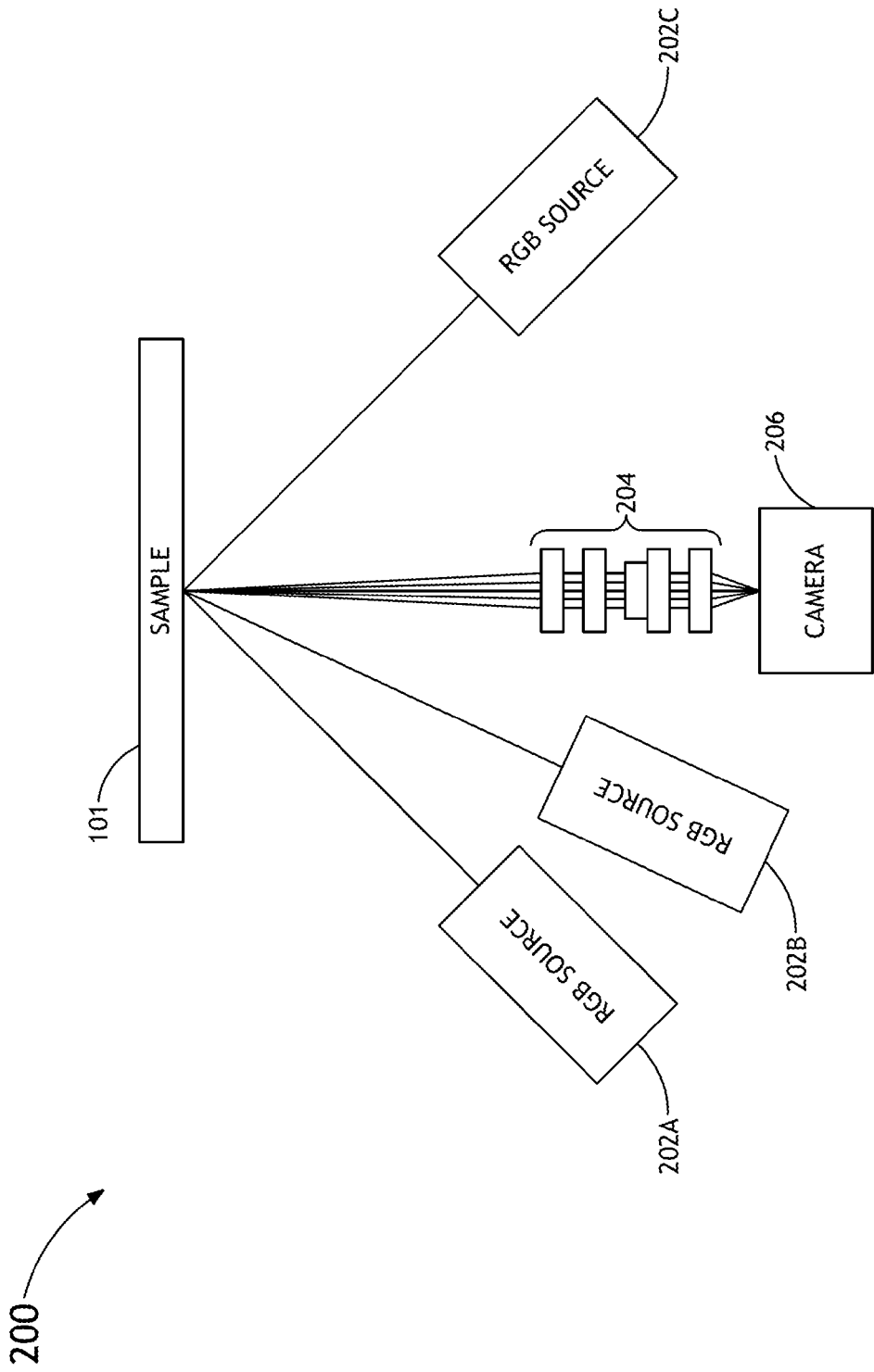
FIG. 2B is a block diagram illustrating a system for inspecting a sample, in accordance with an embodiment of this disclosure.

FIGS. 2A and 2B illustrate various embodiments of an inspection system 200 (i.e. inspection module 200). The inspection module 200 may include a stage 201 configured to support the sample 101. The inspection module 200 may further include one or more illumination sources 202 configured to illuminate a surface of the sample 101. In some embodiments, the one or more illumination sources 202 are configured to illuminate the backside of the sample 101. The illumination sources 202 may include separately controlled red, green, and blue (RGB) sources 202A, 202B, and 202C, such as red, green, and blue LEDs. The RGB sources 202 may be configured to sequentially scan the surface of the sample 101 with red, green, and blue illumination to achieve color separation for bright field (BF) color imaging. In some embodiments, dark field (DF) inspection is completed in a fourth scan succeeding the three RGB scans for BF inspection.

The inspection module 200 may include one or more detectors 206 configured to receive illumination reflected from the surface of the sample 101 through at least one collection path delineated by one or more optical elements 204. In some embodiments, the one or more detectors 206 include a time delay integration (TDI) camera or array. In some embodiments, the RGB color separation allows for a flat fielded image with a monochrome TDI camera or array. The computing system 108 may be configured to receive information (e.g. image frames) associated with the illumination collected by the one or more detectors 206 of the inspection module 200. The computing system 108 may be further configured to determine one or more defect locations based on the information received from the one or more detectors 206.

In some embodiments, the review module 300 may be configured to image one or more portions of the surface of the sample 101 including the one or more located defects after an inspection scan, utilizing information collected via the inspection module 200, or from a stored data file associated with one or more defect locations of the sample 101. In some embodiments, the review images are collected utilizing 0.2 um pixel, diffraction limited visible BF 0.7 NA implementation. In some embodiments, each of the inspection module 200 and the review module 300 is configured to establish wafer coordinates. In some embodiments, the review module 300 is configured to establish wafer coordinates utilizing a laser beam as an edge finder, and the inspection module 200 is configured to establish wafer coordinates utilizing image information.

Figure 3A:
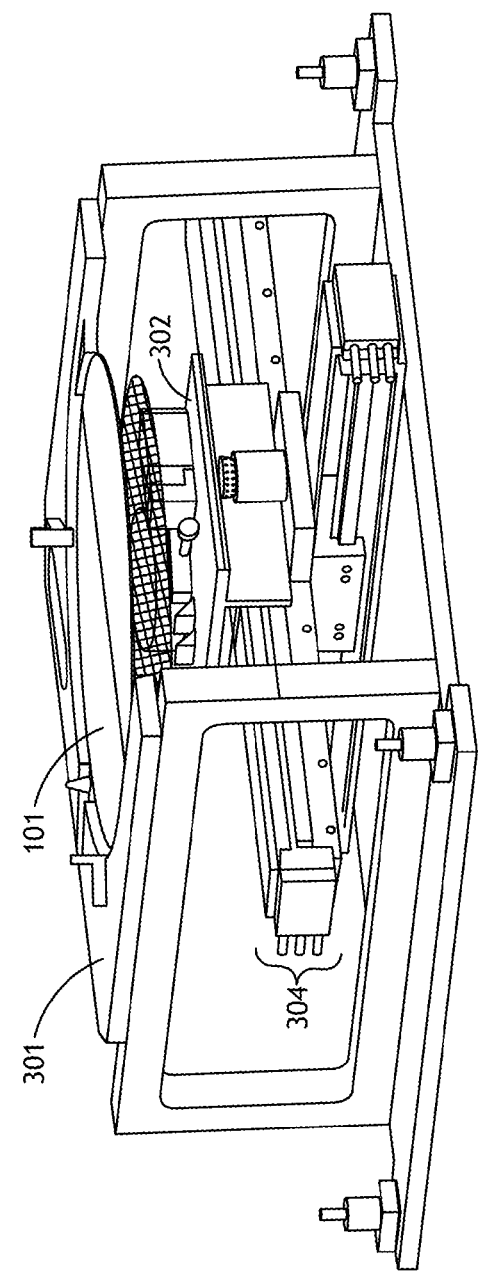
FIG. 3A illustrates a system for reviewing a defect of a sample, in accordance with an embodiment of this disclosure.
Figure 3B:
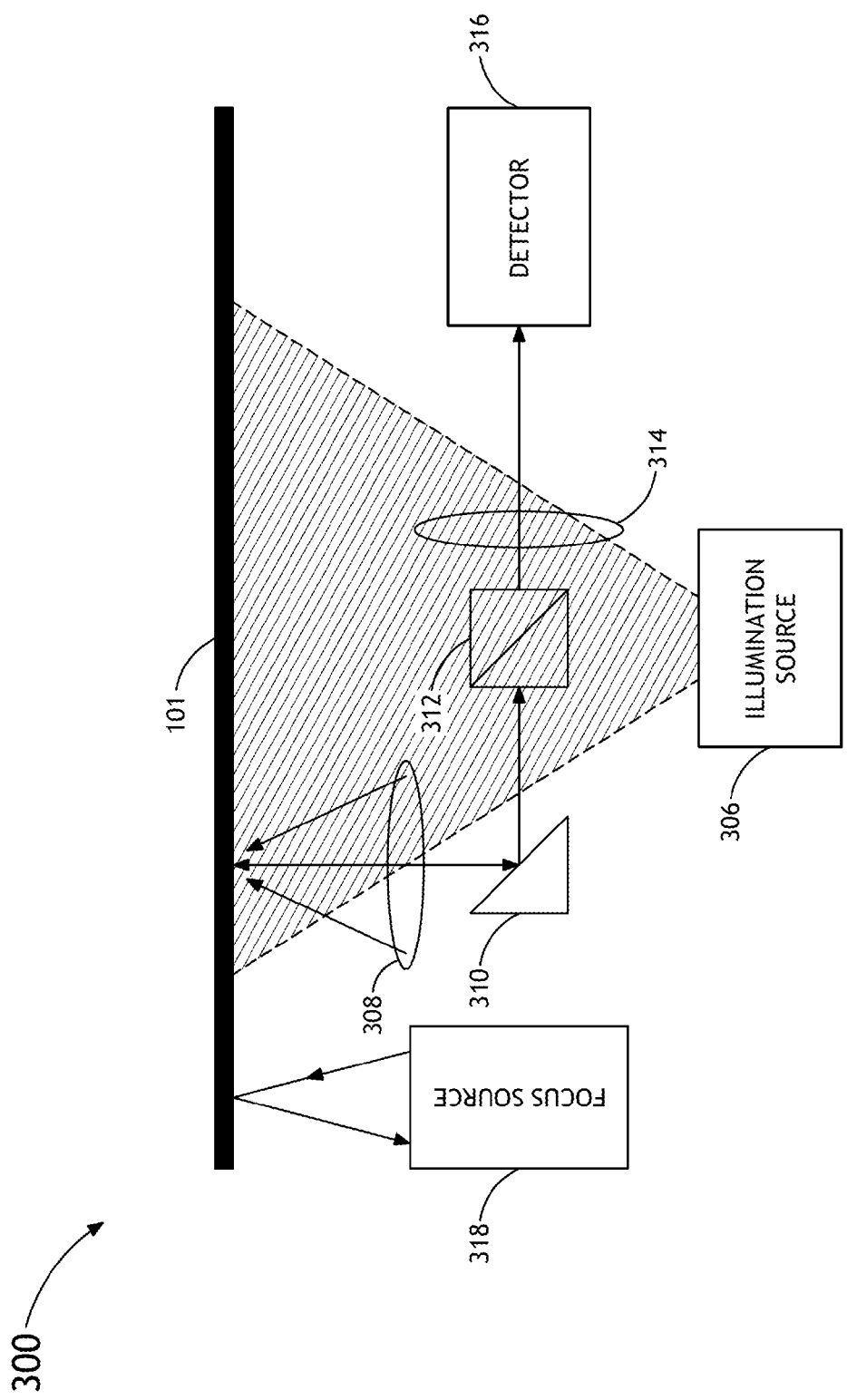
FIG. 3B is a block diagram illustrating a system for reviewing a defect of a sample, in accordance with an embodiment of this disclosure.
Figure 3C:
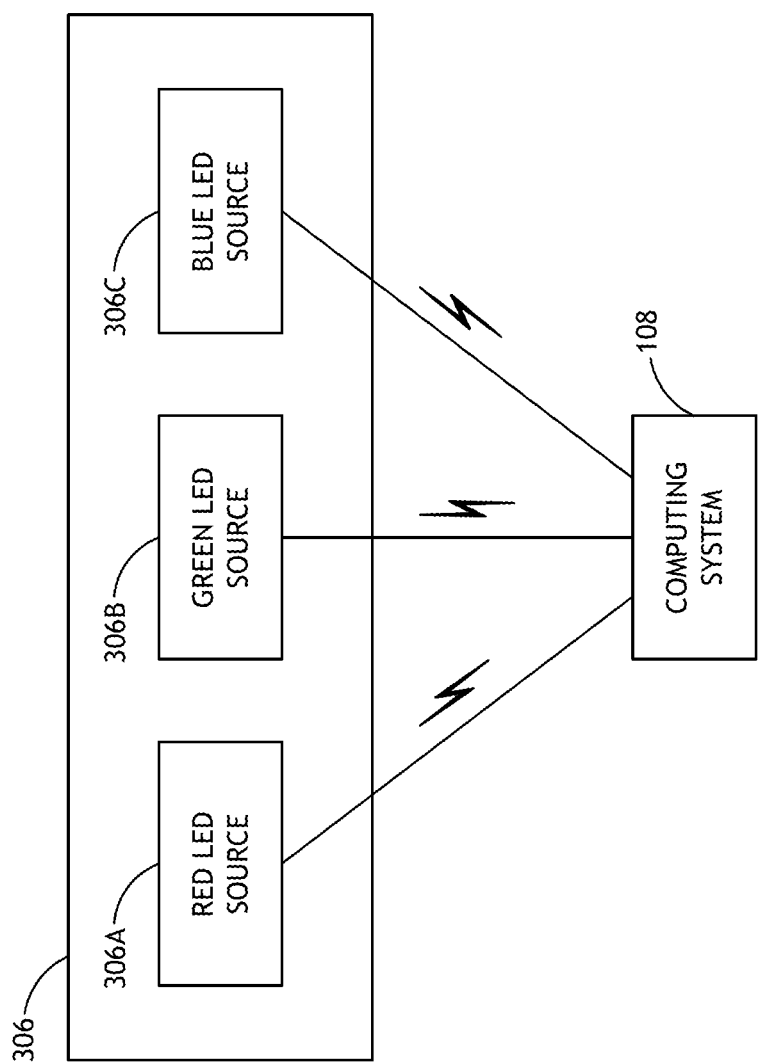
FIG. 3C is a block diagram illustrating one or more pulse width modulated illumination sources, in accordance with an embodiment of this disclosure.

FIGS. 3A through 3C illustrate various embodiments of a review system 300 (i.e. review module 300). The review module 300 may include a stage 301 configured to support the sample 101. In some embodiments, the review module 300 is further configured for backside review of the sample 101. In some embodiments, where the inspection module 200 includes the review module 300, the inspection-review module 200/300 may include one stage 201/301 configured to support the sample 101 for inspection and review. The various imaging components (illustrated in FIG. 3B) of the review module 300 may be supported on a platform 302 coupled to an actuation means 304, such as one or more motors or servos driving a mechanical linkage to actuate the platform 302 to a selected location. In some embodiments, the actuation means 304 includes a stacked two dimensional actuation assembly configured to translate the platform 302 along at least a first axis and a second axis. In some embodiments, the actuation means 304 further includes a Z-axis actuator configured to actuate the platform 304 towards or away from the surface of the sample 101 for focusing.

As illustrated in FIG. 3B, the review module 300 may include at least one illumination source 306 configured to illuminate at least a portion of the surface of the sample 101. At least one detector 316 (e.g. monochrome or polychrome TDI camera) may be configured to receive illumination reflected from a selected (imaged) portion of the surface of the sample 101 to collect review images of one or more sample defects. In some embodiments, the illumination follows an illumination/collection path delineated by optical elements. For example, illumination emanating from the illumination source 306 may flow through a tube lens, beam splitter 312, and objective 308 to the surface of the sample 101. Then illumination reflected from the surface of the sample 101 may flow through a second (off-the-wafer) beam splitter 310 through a tube lens 314 to the detector 316. In some embodiments, the review module 300 further includes a focus sensor 318, such as a laser edge detector, configured to establish wafer coordinates.

As illustrated in FIG. 3C, the illumination source 306 of the review module 300 may include a three-color LED chip with separately controllable red, blue, and green LEDs 306A, 306B, and 306C. The computing system 108 may be configured to directly or indirectly (e.g. via a dedicated source controller) control the RGB sources 306 to sequentially illuminate the imaged portion of the surface of the sample 101 with red, green, and blue illumination to collect at least three separate images utilizing the detector 316. At least one computing system 108 in communication with the detector 316 may be configured to reconstruct a color image utilizing the three monochrome images separately collected utilizing the red, green, and blue illumination.

In some embodiments, the computing system 108 is further configured to correct lateral color utilizing a digital filter. In some embodiments, the detector 316 is configured to shift focus in between image acquisitions for longitudinal color correction. Longitudinal and lateral color correction may be enabled in Bayer and 3-chip camera schemes as well, with multiple image sets. For example, the detector 316 may be configured to collect three color images, and the computing system 108 may be configured to combine the red from image 1, the green from image 2, and the blue from image 3 to construct a color image having a selected level of focus (e.g. best determined focus). In addition, the computing system 108 may be configured to correct lateral color in the color review images utilizing a digital filter. Therefore, the advantages of improved optical quality are not limited to a monochrome camera collection scheme. The review module 300 may include any camera set up (e.g. Bayer, 3-chip, polychrome, or the monochrome system) utilizing the image collection scheme to refocus and correct lateral color, thereby allowing for lower cost optics while still supporting sufficient image quality.

In some embodiments, the RGB color addressable source 306 is configured for white balancing. The detector 316 (e.g. a color camera) may be "white balanced" by turning the gain up in the 2 dimmer colors. This results in more noise in these colors. With independent color control, the integration time of the detector 316 may be adjusted to get substantial well filling, thereby reducing the noise factor in the white balance adjusted (blue and red) channels. Furthermore, utilizing LED sources may increase the flexibility of timing, thereby making strobe or quasi-continuous illumination possible over a selected integration time.

In some embodiments, the one or more illumination sources 202 or 306 of the inspection system 200 and/or the review system 300 are pulse width modulated (PWM) to maintain substantially constant intensity in the presence of stage velocity errors. The integration time (e.g. 1 over the line rate)*the number of TDI lines determines the illumination collection time of the detector 206 or 316. To control the amount of illumination collected by the detector 206/316, the illumination source 202/306 may be configured to operate in PWM mode for a fixed duration after each TDI line trigger. The fixed pulse count method may mitigate inconsistency from fluctuations in stage speed. For example, the detector 206/316 may be configured to receive the approximately equal amounts of illumination at a local velocity of 100 mm/sec and a local velocity of 105 mm/sec. Accordingly, lower cost stages 201/301 may be employed with less chance of intensity ripples in the resulting images. Furthermore, the stage 201/301 may not need to achieve a constant velocity before intensity of illumination is stabilized. The foregoing advantage may be critical in systems, such as the inspection system 200 and review system 300 described herein, where a limited length of stage travel is allowed.

In some embodiments, the computing system 108 is configured to directly or indirectly (e.g. via an LED controller) drive the one or more illumination sources 202/306 to send a trigger stream of illumination pulses out at the occurrence of each TDI line sync received (e.g. based upon stage encoder position). Accordingly, the illumination sources 202/306 may be configured to provide a selected (i.e. adjustable) burst length over every N line synchs for higher precision and lower overall achievable image light level. In some embodiments, the illumination sources 202/306 are configured to sequentially delay the burst of illumination pulses with each line synch to avoid changes in the "TDI blur" with imaging for variation in burst length between systems. Doing so effectively adds illumination at all possible positions in the TDI time delay smear.

Figure 4:
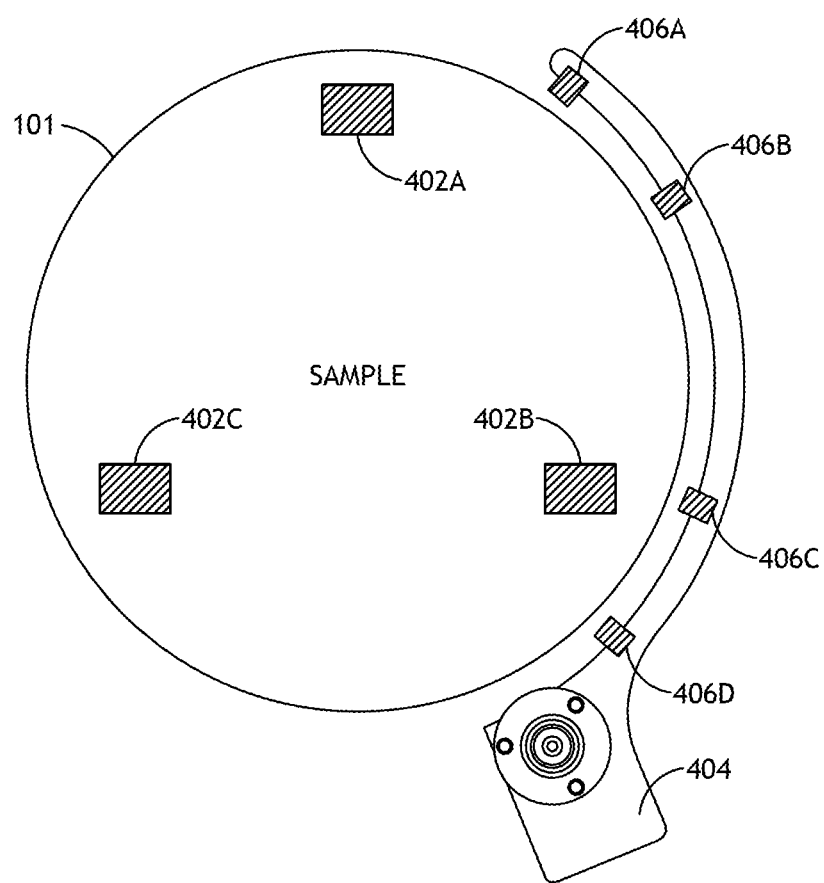
FIG. 4 illustrates a wafer supported by at a plurality of selected points and stabilized utilizing a sidearm, in accordance with an embodiment of this disclosure.

In some embodiments, the inspection system 200 and/or the review system 300 may include mechanisms for mitigating imaging errors due to sample motion (e.g. vibration, oscillation, velocity changes). FIG. 4 illustrates a stage assembly 400 for analyzing a first surface (e.g. backside) of the sample 101 without harmful contact with a second surface (e.g. front side) of the sample 101. In some embodiments, stages 201 or 301 include the stage assembly 400 described herein.

The stage assembly 400 may include a selected number (e.g. at least 3) of chucks 402 configured to support the sample 101. In some embodiments, the chucks 402 are configured to contact the sample 101 at points near the edge of the sample 101 such that the supported surface (e.g. wafer backside) is substantially accessible to illumination. In some embodiments, the chucks 402 are supported by at least one mechanical linkage coupled to an actuator configured to actuate the support chucks 402 to one or more contact points proximate to the imaged portion of the surface of the sample 101. Accordingly, effectively rigid force may be applied around the imaged portion of the sample 101 to deflect undesired motion.

The stage assembly 400 further includes at least one side arm 404 with a plurality of vertical contact friction points 406 configured to contact an edge of the sample 101 to reduce sample motion. In some embodiments, supporting the sample edges through friction (e.g. with a spring contact force of approximately 1 Newton) serves to reduce the oscillation at the edges by a significant factor (e.g. factor of 5 to 10, depending on the number of edge contact points). In some embodiments, the stage assembly 400 includes two side arms 404 contacting points long both halves of the sample 101. In some embodiments, the one or more side arms 404 further include a reciprocating mechanism (e.g. spring) configured to dampen sample motion.

Typical acoustic driven oscillations with a 3-point support in a fan filter unit 104 environment see on the order of 5 um amplitude vibration oscillation in the 40 to 60 Hz frequency range. One method of mitigating imaging errors due to the oscillations is to strobe the LED light source 202/306. An algorithm may incorporate lead/lag, velocity direction, and knowledge of current peaks to avoid phase lag in the "real time" focus position monitor compared to the real time position. While this method of strobing can collect in focus images, it is preferable to reduce the magnitude of the target focus oscillation. For a given defocus range, the strobe duration is reduced with greater oscillation amplitude and errors in position sensing with focus sensor latency increase. Accordingly, the stage assembly 400 may be employed in conjunction with strobed sources 202/306 to reduce oscillation of the sample 101.

Figure 5:
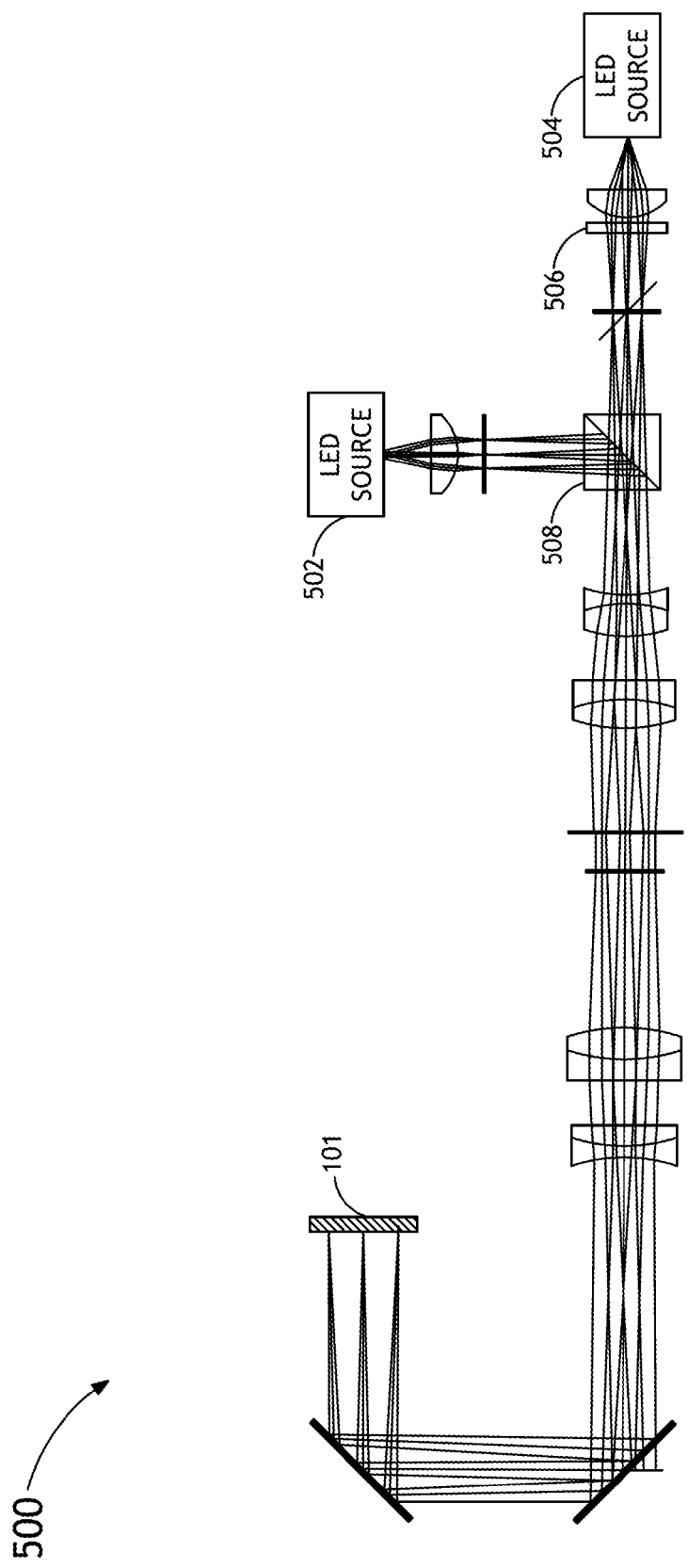
FIG. 5 is a block diagram illustrating a system for analyzing a sample with a secondary path for focusing one or more detectors of the system, in accordance with an embodiment of this disclosure.

FIG. 5 illustrates a system 500 for focusing one or more detectors, such as detectors 206/316 of the inspection system 200 and/or the illumination system 300. The system 500 includes a first illumination source 502 configured to provide illumination along a first (imaging) path and a second illumination source 504 configured to provide illumination along a second (focusing path). In some embodiments, the illumination sources 502 and 504 include LEDs having comparable specifications. The first illumination source 502 and the second illumination source 504 may be operated separately to either collect an image of a selected portion of the sample 101 or to project a grid mask 506 to process focus. In some embodiments, the imaging path and the focusing path are merged into a common delivery path by a beam splitter 508 disposed after the grid mask 506 of the focusing path. By providing two separate paths, the system 500 may be configured for full field of view focusing across a substantially entirety of the imaging plane.

In some embodiments, the system 500 is configured to determine focus utilizing the second illumination source 504 for single frame projected grid mask image based autofocus (IBFA). In some embodiments, the system 500 is configured to determine a normalized reflection of the surface of the sample 101 utilizing the first illumination source 502, and then configured to collect a second image of the projected grid mask 506 utilizing the second illumination source 504. The system 500 may be further configured to correct the grid mask image with normalization or "don't process" zones near high frequency object regions and to continue processing the projected grid mask corrected image to determine focus. In some embodiments, the focus may corrected by moving an objective on a Z-stage before collecting sample image(s).

Although the foregoing embodiments are described with reference to an inspection system 200 and/or a review system 300, it is contemplated that various systems and methods described herein may be extended to alternative applications, such as semiconductor metrology or other forms of sample analysis known to the art.

It should be recognized that the various steps and functions described throughout the present disclosure may be carried out by a single computing system or by multiple computing systems. The one or more computing systems may include, but are not limited to, a personal computing system, mainframe computing system, workstation, image computer, parallel processor, or any other device known in the art. In general, the term "computing system" may be broadly defined to encompass any device having one or more processors, which execute instructions from at least one carrier medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for analyzing a sample, comprising:
   an inspection module including one or more inspection illumination sources configured to sequentially illuminate a backside surface of the sample with red, green, and blue illumination, and one or more monochromic detectors configured to receive illumination reflected from the backside surface of the sample in response to the sequential illumination by the one or more inspection illumination sources, wherein the one or more inspection illumination sources and the one or more monochromic detectors are positioned below the backside surface of the sample;
   a review module including one or more review illumination sources different from the one or more inspection illumination sources, wherein the one or more review illumination sources are configured to illuminate the backside surface of the sample at a location of one or more defects identified by the inspection module, the review module including one or more detectors configured to receive illumination reflected from the backside surface of the sample in response to the illumination by the one or more review illumination sources;
   a stage assembly configured to support the sample by contacting three or more pre-determined points on the backside surface of the sample and by contacting one or more pre-determined points along an edge of the sample, wherein the edge of the sample is substantially orthogonal to the backside surface of the sample, the three or more pre-determined points identified to minimize obstruction of the backside surface during illumination; and
   at least one computing system including one or more processors in communication with the inspection module and the review module, the at least one computing system configured to determine a location of a defect on the backside of the sample utilizing information associated with the illumination received by the one or more monochromic detectors of the inspection module, and further configured to receive an image of a portion of the backside surface of the sample including the one or more defects utilizing the one or more detectors of the review module and the determined location of the one or more defects.

2. The system of claim 1, wherein the review module further includes:
   a platform configured to support the one or more detectors and collection optics of the review module, wherein the collection optics are configured to direct illumination received from the backside surface of the sample along a collection path to the one or more detectors of the review module; and
   at least one actuator mechanically coupled to the platform, the at least one actuator configured to actuate the platform to a selected location.

3. The system of claim 2, wherein the at least one actuator is configured to translate the platform along a first axis and at least a second axis.

4. The system of claim 1, wherein the one or more review illumination sources are configured to sequentially illuminate the backside surface of the sample with red, green, and blue illumination, and the at least one computing system is configured to reconstruct a color image of the portion of the backside surface of the sample from a first image associated with the red illumination, a second image associated with the green illumination, and a third image associated with the blue illumination collected utilizing the one or more detectors of the review module.

5. The system of claim 4, wherein the one or more detectors of the review module include a monochrome camera.

6. The system of claim 4, wherein the one or more detectors of the review module are configured to collect the first, second, and third images at different focus levels from one another.

7. The system of claim 4, wherein the one or more review illumination sources are configured to provide illumination according to a selected integration time.

8. The system of claim 1, wherein the one or more review illumination sources comprise one or more pulse width modulated light emitting diodes (LEDs).

9. The system of claim 8, wherein the one or more LEDs are configured to provide a plurality of illumination pulses according to a collection time of the one or more detectors of the review module.

10. The system of claim 8, wherein the one or more LEDs are configured to provide the plurality of illumination pulses over a selected number of integration lines associated with the collection time of the one or more detectors of the review module.

11. The system of claim 8, wherein the one or more LEDs are configured to provide a first plurality of illumination pulses and at least a second plurality of illumination pulses sequentially delayed with respect to one another according to the collection time of the one or more detectors of the review module.

12. The system of claim 1, wherein the stage assembly includes at least one sidearm configured to contact the one or more pre-determined points along the edge of the sample.

13. The system of claim 12, wherein the at least one sidearm includes a reciprocating mechanism configured to reduce motion of the sample.

14. The system of claim 1, further comprising:
   an actuator configured to actuate the stage assembly to contact the three or more pre-determined points on the backside surface.

15. The system of claim 1, wherein the one or more review illumination sources of the review module are configured to strobe illumination to compensate for motion of the sample.

16. The system of claim 1, wherein the one or more review illumination sources of the review module include:
   a first illumination source configured to provide illumination along a first illumination path to the backside surface of the sample; and
   a second illumination source configured to provide illumination along a second illumination path to the backside surface of the sample, the second illumination path including a grid mask, wherein the at least one computing system is configured to determine a focus position based upon a portion of illumination from the second illumination source reflected from the backside surface of the sample to the one or more detectors of the review module.

17. The system of claim 16, wherein the first illumination path and the second illumination path merge into a common illumination path leading to the backside surface of the sample.

18. The system of claim 16, wherein the first illumination path is an imaging path and the second illumination path is an image based autofocus path.

19. The system of claim 1, further comprising a frame configured to support the inspection module, the review module, and the at least one computing system.

20. A system for analyzing a sample, comprising:
one or more illumination sources configured to sequentially illuminate a backside surface of the sample with red, green, and blue illumination;
one or more detectors configured to receive illumination reflected from the backside surface of the sample in response to the illumination by the one or more illumination sources, wherein the one or more detectors are configured to collect first, second, and third light-based images at different focus levels from one another, wherein the one or more illumination sources and the one or more detectors are positioned below the backside surface of the sample;
a stage assembly configured to support the sample by contacting three or more pre-determined points on the backside surface of the sample and by contacting one or more pre-determined points along an edge of the sample, wherein the edge of the sample is substantially orthogonal to the backside surface of the sample, the three or more pre-determined points identified to minimize obstruction of the backside surface during illumination; and
at least one computing system including one or more processors in communication the one or more detectors, the at least one computing system configured to reconstruct a color image of a portion of the backside surface of the sample from a first image associated with the red illumination, a second image associated with the green illumination, and a third image associated with the blue illumination collected utilizing the one or more detectors, wherein the at least one computing system is further configured to perform at least one of lateral color correction or longitudinal color correction.

21. The system of claim 20, wherein the one or more detectors include a monochrome camera.

22. The system of claim 20, wherein the one or more illumination sources are configured to provide illumination according to a selected integration time.

23. The system of claim 20, wherein the one or more illumination sources comprise one or more pulse width modulated light emitting diodes (LEDs).

24. The system of claim 23, wherein the one or more LEDs are configured to provide a plurality of illumination pulses according to a collection time of the one or more detectors.

25. The system of claim 23, wherein the one or more LEDs are configured to provide the plurality of illumination pulses over a selected number of integration lines associated with the collection time of the one or more detectors.

26. The system of claim 23, wherein the one or more LEDs are configured to provide a first plurality of illumination pulses and at least a second plurality of illumination pulses sequentially delayed with respect to one another according to the collection time of the one or more detectors.

27. A system for analyzing a sample, comprising:
a stage assembly configured to support the sample by contacting three or more pre-determined points on the backside surface of the sample and by contacting one or more pre-determined points along an edge of the sample, wherein the edge of the sample is substantially orthogonal to the backside surface of the sample, the three or more pre-determined points identified to minimize obstruction of the backside surface during illumination;
one or more illumination sources configured to illuminate the backside surface of the sample with light, wherein the one or more illumination sources are configured to strobe the light to compensate for motion of the sample by varying the intensity output of the one or more illumination sources;
one or more detectors configured to receive light reflected from the backside surface of the sample in response to the light by the one or more illumination sources, wherein the one or more illumination sources and the one or more detectors are positioned below the backside surface of the sample; and
at least one computing system in communication the one or more detectors, the at least one computing system configured to determine information associated with a defect of the sample utilizing information associated with the light received by the one or more detectors.

28. The system of claim 27, wherein the backside surface of the sample comprises a backside of a wafer, wherein the backside of the wafer is substantially accessible to light from the one or more illumination sources.

29. The system of claim 27, wherein the stage assembly includes at least one sidearm configured to contact the one or more pre-determined points along the edge of the sample.

30. The system of claim 29, wherein the at least one sidearm includes a reciprocating mechanism configured to reduce motion of the sample.

31. The system of claim 29, wherein the at least one sidearm comprises a first sidearm and a second sidearm.

32. The system of claim 27, further comprising:
an actuator configured to actuate the stage assembly to contact the three or more pre-determined points at one or more selected locations of the backside surface of the sample.

33. A system for analyzing a sample, comprising:
a first light source configured to provide illumination along a first illumination path to a backside surface of the sample;
a second light source configured to provide illumination along a second illumination path to the backside surface of the sample, the second illumination path including a grid mask, wherein at least one of the first light source or the second light source includes one or more light emitting diodes;
one or more detectors configured to receive illumination reflected from the backside surface of the sample in response to the illumination from at least one of the first light source and the second light source, wherein the first light source, the second light source, and the one or more detectors are positioned below the backside surface of the sample;
a stage assembly configured to support the sample by contacting three or more pre-determined points on the backside surface of the sample and by contacting one or more pre-determined points along an edge of the sample, wherein the edge of the sample is substantially orthogonal to the backside surface of the sample, the three or more pre-determined points identified to minimize obstruction of the backside surface during illumination; and
at least one computing system in communication the one or more detectors, the at least one computing system configured to determine a focus position based upon a portion of illumination from the second illumination source reflected from the backside surface of the sample to the one or more detectors.

34. The system of claim 33, wherein the first illumination path and the second illumination path merge into a common illumination path leading to the backside surface of the sample.

35. The system of claim 33, wherein the first illumination path is an imaging path and the second illumination path is an image based autofocus path.

* * * * *